US009126043B2

(12) United States Patent
Kaula et al.

(10) Patent No.: US 9,126,043 B2
(45) Date of Patent: Sep. 8, 2015

(54) PATIENT HANDHELD DEVICE FOR USE WITH A SPINAL CORD STIMULATION SYSTEM

(75) Inventors: Norbert Kaula, Arvada, CO (US); Yohannes Iyassu, Denver, CO (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 13/118,781

(22) Filed: May 31, 2011

(65) Prior Publication Data

US 2012/0310305 A1   Dec. 6, 2012

(51) Int. Cl.
   *A61N 1/36* (2006.01)

(52) U.S. Cl.
   CPC ........ *A61N 1/36071* (2013.01); *A61N 1/36132* (2013.01)

(58) Field of Classification Search
   CPC ........... A61N 1/36071; A61N 1/36132; A61N 1/37217
   USPC .......................................... 607/46, 57, 59–62
   See application file for complete search history.

(56) References Cited

U.S. PATENT DOCUMENTS

| 7,881,805 B2 | 2/2011 | Bradley et al. |
| 2001/0034542 A1 | 10/2001 | Mann |
| 2006/0058627 A1 | 3/2006 | Flaherty et al. |
| 2006/0293720 A1 | 12/2006 | DiLorenzo |
| 2007/0032834 A1 | 2/2007 | Gliner et al. |
| 2007/0167991 A1 | 7/2007 | DiLorenzo et al. |
| 2009/0018617 A1 | 1/2009 | Skelton et al. |
| 2009/0105787 A1 | 4/2009 | Kokones et al. |
| 2010/0331921 A1 | 12/2010 | Bornzin et al. |
| 2011/0093089 A1* | 4/2011 | Martin ............................ 623/24 |
| 2012/0192874 A1* | 8/2012 | Bolea et al. ................... 128/848 |

FOREIGN PATENT DOCUMENTS

WO   03/051175   6/2003

OTHER PUBLICATIONS

European Search Report for Application No. 12169536.5 dated Sep. 28, 2012 (10 pages).
Freescale Semiconductor, Inc., "i.MX51 Applications Processors for Consumer and Industrial Products," Data Sheet: Technical Data, Document No. IMX51CEC, Rev. 4 (Aug. 2010) 200 pages.
North, R.B. et al., "Patient-interactive, computer-controlled neurological stimulation system: clinical efficacy in spinal cord stimulator adjustment," J. Neurosurg. (1992) 76(6):967-972, http://www.ncbi.nlm.nih.gov/pubmed/1588431.
Texas Instruments Inc., "Mixed Signal Microcontroller," brochure, MSP430G2x32, MSP430G2x02; SLAS723 (Dec. 2010) 53 pages.
Virtualmedicalcentre.com, "Spinal Cord Stimulation Devices," http://www.virtualmedicalcentre.com/devices.asp?sid=2 (Nov. 1, 2008) 7 pages.

* cited by examiner

*Primary Examiner* — Catherine Voorhees
(74) *Attorney, Agent, or Firm* — Haynes & Boone, LLP

(57) ABSTRACT

A patient feedback device for communicating with a programming device of an electrical stimulation system. The device includes a housing, a sensor, a controller, and a communication port. The sensor is supported by the housing and generates a sensor signal in response to an action from the patient. The controller is supported by the housing and is in operative communication with the sensor. The controller receives the sensor signal and sends information to the communication port based on the sensor signal. The communication port is connected to the housing and is in operative communication with the controller. The communication port receives information from the controller and wirelessly transmits a communication signal to the programming device of the electrical stimulation system.

23 Claims, 6 Drawing Sheets

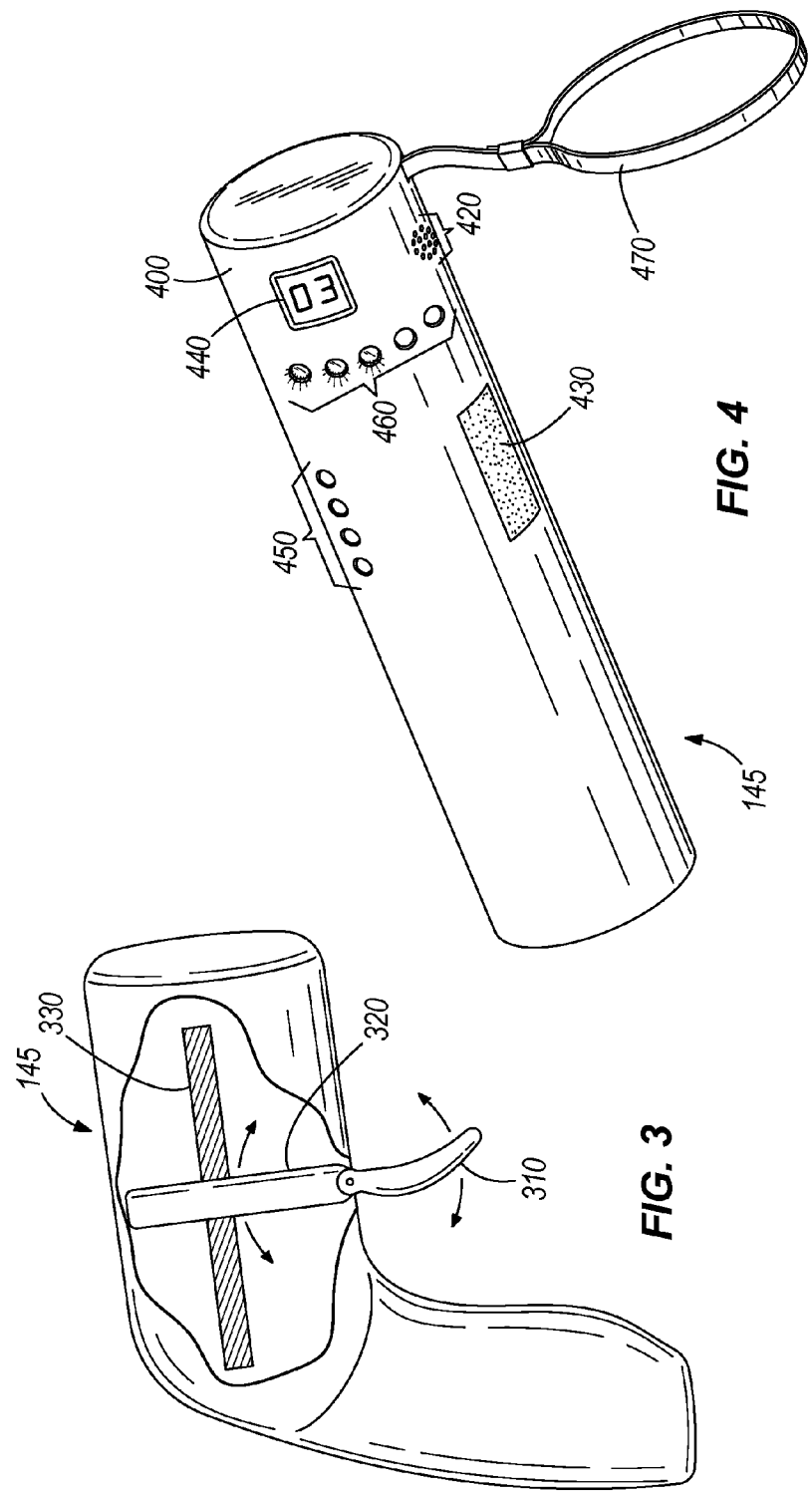

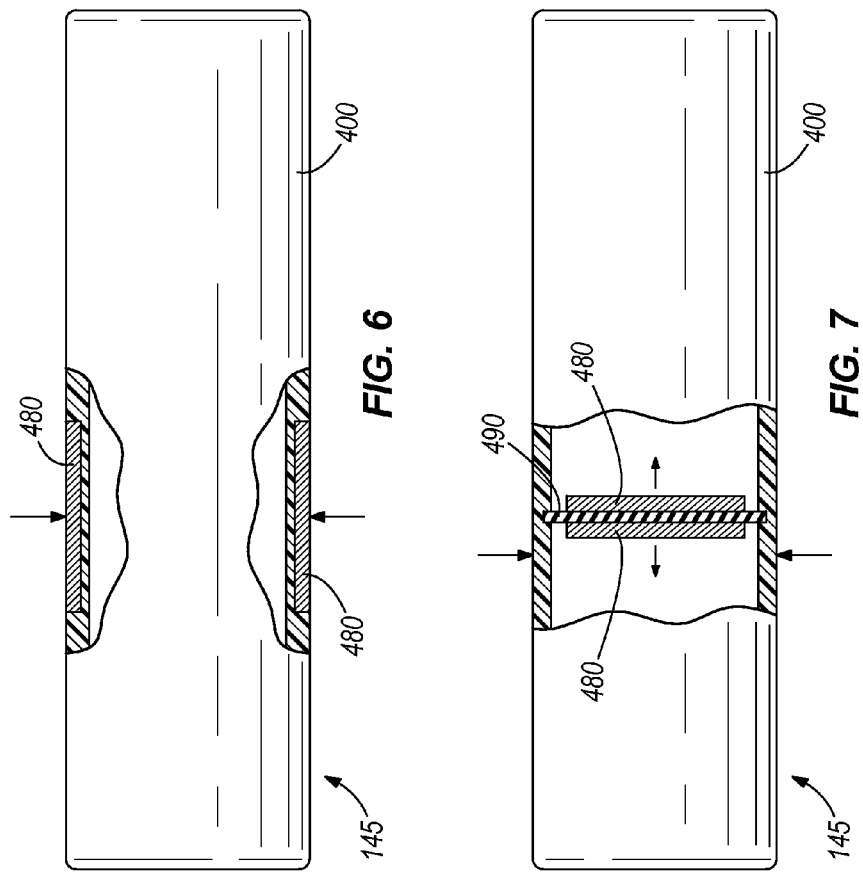
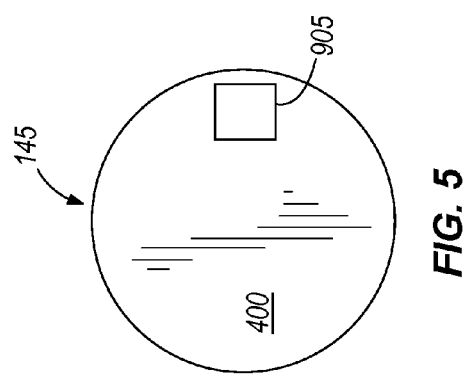
FIG. 5
FIG. 6
FIG. 7

PATIENT HANDHELD DEVICE FOR USE WITH A SPINAL CORD STIMULATION SYSTEM

BACKGROUND

The invention relates to a patient handheld device for a stimulation system, such as a spinal cord stimulation (SCS) system, and in particular to a handheld device that a patient can use to provide feedback during programming of an electrical stimulation generator, such as an implantable pulse generator (IPG).

A spinal cord stimulator is a device used to provide electrical stimulation to the spinal cord or spinal nerve neurons for managing pain. The stimulator includes an implanted or external pulse generator and an implanted medical electrical lead having one or more electrodes at a distal location thereof. The pulse generator provides the stimulation through the electrodes via a body portion and connector of the lead. Spinal cord stimulation programming is defined as the discovery of the stimulation electrodes and parameters that provide the best possible pain relief (or paresthesia) for the patient using one or more implanted leads and its attached IPG. The programming is typically achieved by selecting individual electrodes and adjusting the stimulation parameters, such as the shape of the stimulation waveform, amplitude of current in mA (or amplitude of voltage in V), pulse width in microseconds, frequency in Hz, and anodic or cathodic stimulation.

With newer medical electrical leads having an increased number of electrodes, the electrode and parameter combination increases exponentially. This results in a healthcare professional, such as a clinician, requiring a substantial amount of time for establishing a manually created protocol for providing therapeutic spinal cord stimulation. Therefore, a manual approach for creating a protocol is not an optimal solution for the SCS system.

SUMMARY

Numerous embodiments of the invention provide a method and system for programming an SCS system with a substantially reduced time requirement and increased accuracy. More specifically, in numerous embodiments, a sweep process is used with the electrodes of an implanted medical lead to determine the proper SCS program (also referred to herein as an SCS protocol) for providing the best possible pain relief for the patient. In other embodiments, a sweep process can be used on a single electrode by varying a pulse width, frequency, or amplitude applied to the single electrode, for example. It is also envisioned that other sweep processes are possible, such as combinations of the above sweep processes.

Thus, in one aspect the invention provides a patient feedback device for communicating with a programming device of an electrical stimulation system. The device includes a housing, a sensor, a controller, and a communication port. The sensor is supported by the housing and generates a sensor signal in response to an action from the patient. The controller is supported by the housing and is in operative communication with the sensor. The controller receives the sensor signal and sends information to the communication port based on the sensor signal. The communication port is connected to the housing and is in operative communication with the controller. The communication port receives information from the controller and wirelessly transmits a communication signal to the programming device of the electrical stimulation system.

In another aspect the invention provides a method of providing patient feedback to a programming device of an electrical stimulation system with a patient feedback device, where the patient feedback device includes a housing having a sensor, a controller, and a communication port connected thereto and the controller is in operative communication with the sensor and the communication port. The sensor detects a force, a distance traveled, or other impetus applied by the patient in response to a stimulus received by the patient. The sensor generates a signal in response to the applied impetus. The controller receives the signal generated by the sensor. The controller sends information to the communication port based on the signal. The communication port transmits a signal to the programming device.

In still another aspect the invention provides a patient feedback device for communicating with a programming device of an electrical stimulation system. The device includes a resilient housing, a sensor, a controller, and a communication port. The sensor is supported by the housing and generates a sensor signal in response to an impetus applied to the housing by the patient. The controller is supported by the housing and is in operative communication with the sensor. The controller receives the sensor signal and sends information to the communication port based on the sensor signal. The communication port is connected to the housing and is in operative communication with the controller. The communication port receives information from the controller and transmits a communication signal to the programming device of the electrical stimulation system.

In yet another aspect the invention provides a method of calibrating a patient feedback device for use in an electrical stimulation system, where the system includes an implantable pulse generator (IPG) implanted in a patient and a patient feedback device having a force sensor. The method includes steps of: sensing input from the patient using the patient feedback device; at a first time, applying an electrical stimulus with the IPG; monitoring the force sensor at a plurality of time points; recording a level of force sensed by the force sensor at each of the plurality of time points; identifying at least one of a time point at which a maximum force is applied and a time point at which a minimum force is applied; and comparing the first time to at least one of the time point at which a minimum force is applied and the time point at which a maximum force is applied to determine a patient response time.

Other aspects of the invention will become apparent by consideration of the detailed description and accompanying drawings.

BRIEF DESCRIPTION OF THE DRAWINGS

FIG. 3 is a partial cutaway view of a patient feedback device employing an isotonic force sensor.

FIG. 4 is a perspective view of a patient feedback device employing an isometric force sensor.

FIG. 5 is a perspective view of a patient feedback device employing a pressure sensor.

FIG. 6 is a cross-sectional view of a patient feedback device employing strain gauge elements.

FIG. 7 is a cross-sectional view of a patient feedback device employing strain gauge elements.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other constructions and of being practiced or of being carried out in various ways.

The invention herein relates to an electrical stimulation system for providing stimulation to a target tissue of a patient. The electrical stimulation system includes a patient-feedback device (PFD) 145. In the construction shown, the PFD 145 is for use with a spinal cord stimulation (SCS) system 100, which provides electrical pulses to a patient, including to the neurons of the spinal cord and/or sacrum of a patient. Other electrical stimulation systems provide electrical pulses to other portions of a patient's body including a muscle or muscle group, peripheral nerves, the brain, etc.

In various implementations, the PFD 145 is used in conjunction with a clinician programmer (CP) 130 to program an implantable pulse generator (IPG) 115 for a patient. The IPG 115 communicates with any one of the CP 130, a patient programmer and charger (PPC) 135, and a pocket (or fob) programmer (PP) 140. As discussed in further detail below, the CP 130 interacts with the IPG 115 to develop a program (or protocol) for stimulating the patient, which may be facilitated through the use of the PFD 145. Once a protocol is developed by the CP, the PPC 135 or the PP 140 can activate the protocol. The protocol may be stored at the IPG 115 or can be communicated and stored at the PPC 135 or the PP 140. The PPC 135 also is used for charging the IPG 115. Constructions of the IPG 115, CP 130, PPC 135, and PP 140 are disclosed in U.S. patent application Ser. No. 13/118,775 (US Pat. Appl. Publ. No. 2012/031300) and Ser. No. 13/118,764 (US Pat. Appl. Publ. No. 2012/031299), both of which are filed on even date herewith and are entitled "SYSTEM AND METHOD OF ESTABLISHING A PROTOCOL FOR PROVIDING ELECTRICAL STIMULATION WITH A STIMULATION SYSTEM TO TREAT A PATIENT", and both of which are incorporated herein by reference.

Figure 1:
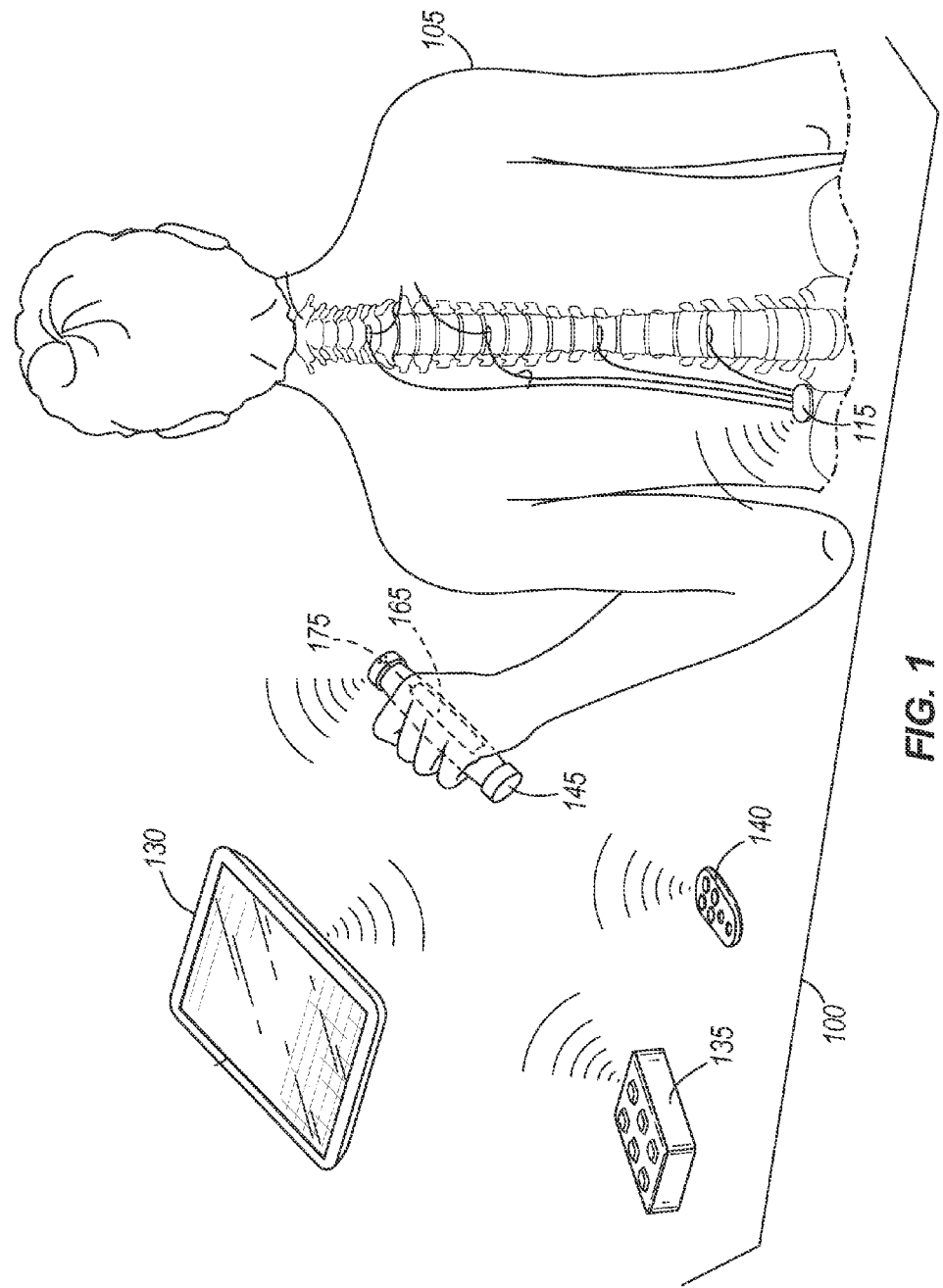
FIG. 1 is a partial perspective view of a patient using a spinal cord stimulation system.

Referring back to FIG. 1, a user may provide feedback to the CP 130 with the PFD 145 while the CP 130 develops the protocol for the IPG 115. In the construction shown in FIG. 1, the PFD 145 is an ergonomic handheld device having a sensor (also referred to as input) 165, a controller, and a communications output 175. The sensor 165 can include a discrete switch and/or a continuously variable input, such as through the use of a thermocouple, strain gauge, pressure sensor, 905 (FIG. 5) piezoelectric device, accelerometer, displacement mechanism, or other variable sensing mechanism. It is envisioned that the use of a continuously variable input can provide magnitude information, thereby providing improved feedback information from the patient.

In use, the CP 130 activates one or more of the electrodes of the IPG 115 in various patterns. When the patient 105 feels a sensation as a result of a stimulus, such as a stimulus for paresthesia, he or she activates a sensor on the PFD 145. The activation of the sensor indicates to the system 100 that the patient 105 felt the stimulus and can also convey the degree of sensation that is felt, depending on the type of sensor that is employed. Given that there may be a delay from the time the patient 105 feels a sensation and activates the sensor, the system 100 then re-stimulates the most recently-activated combinations of electrodes and the patient 105 again uses the PFD 145 to indicate when (and to what degree) a sensation is felt in order to determine the combination of electrodes to which the patient 105 was reacting. Further description of methods for use of the IPG 115, CP 130, PPC 135, PP 140, and PFD 145 are disclosed in U.S. patent application Ser. Nos. 13/118,775 and 13/118,764, both of which were incorporated by reference above.

Figure 2:
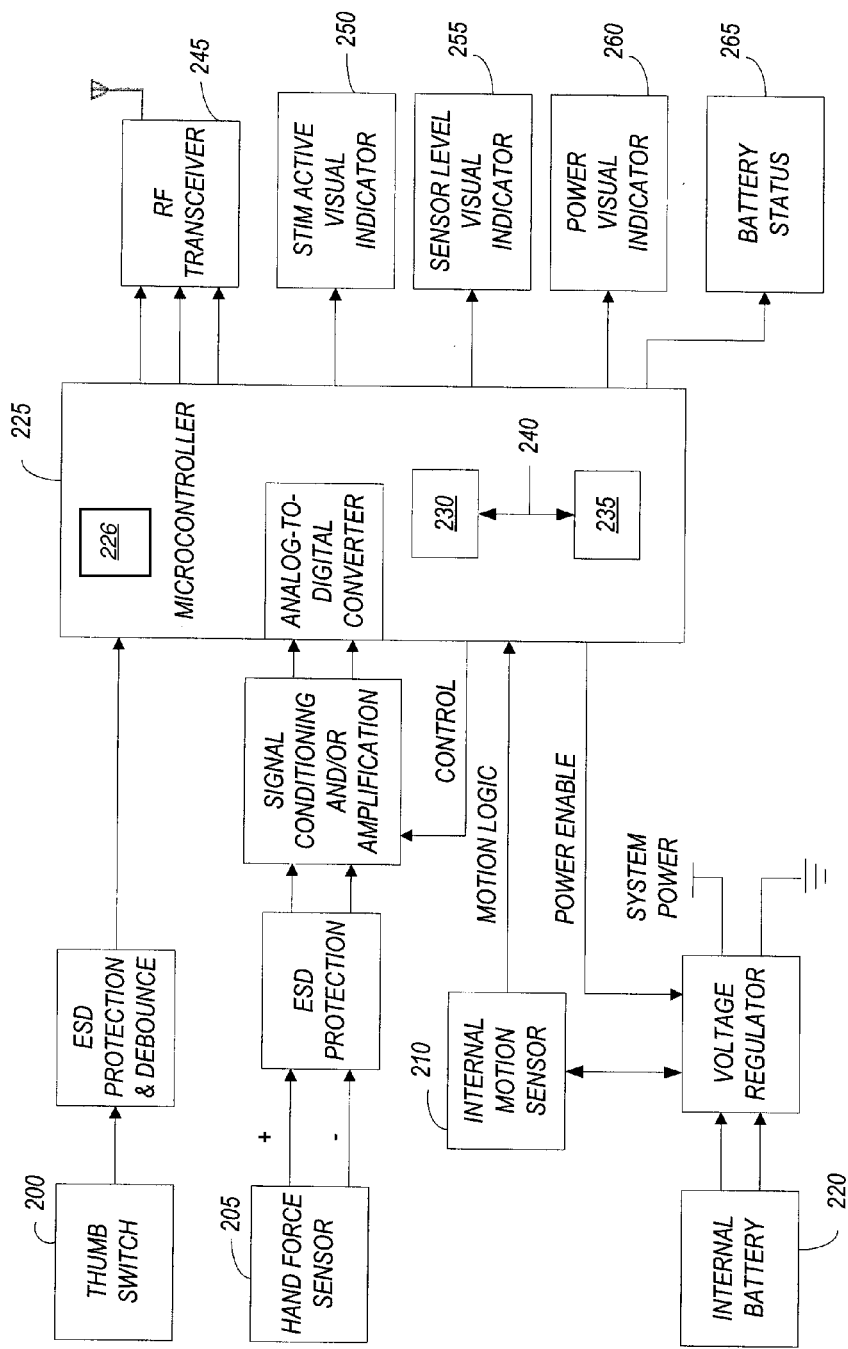
FIG. 2 is a block diagram of a patient-feedback device for use in the spinal cord stimulation system of FIG. 1.

FIG. 2 provides a block diagram of an exemplary handheld PFD 145 for use in the SCS system 100. In various constructions, the PFD 145 includes a housing 400 which may have one or more of a sensor, a controller, and/or a communication port connected thereto. The construction of the PFD 145 shown in FIG. 2 includes two inputs 200 and 205 in communication with the housing 400 of the device 145 and one input 210 internal to the housing 400. One of the external inputs 200 is a binary ON/OFF switch, preferably activated by the patient's thumb, to allow the patient 105 to immediately deactivate stimulation. Input 200 may be coupled to the controller 225 via electrostatic discharge (ESD) protection and/or debouncing circuits. The second input 205 includes a force sensor sensing the pressure or force exerted by the patient's hand. Input/sensor 205 may be coupled to the controller 225 via ESD protection, signal conditioning, and/or signal amplification circuits. The sensed parameter can be either isotonic (constant force, measuring the distance traversed) or isometric (measured force, proportional to pressure applied by patient 105). The resulting signal from the sensor 205 is analog and, therefore, after the signal is conditioned and/or amplified, it can be passed to microcontroller 225 via an analog-to-digital converter.

The internal input 210 for the PFD 145 of FIG. 2 is a motion sensor. The sensor 210, upon detecting motion, initiates activation of the PFD 145. The device 145 stays active until movement is not detected by the sensor 210 for a time period, which in various constructions may be between one second and five minutes. Power is provided by an internal battery 220 that can be replaceable and/or rechargeable, which in various constructions has an approximately three hour life under continuous use. As discussed below, a motion sensor such as sensor 210 can also be used to obtain feedback from the patient 105 regarding paresthesia.

The processing of the inputs from the sensors 200 and 205 takes place in a controller, such as a microcontroller 225. An exemplary microcontroller capable of being used with the invention is microcontroller 225, which includes a suitable programmable portion 230 (e.g., a microprocessor or a digital signal processor), a memory 235, and a bus 240 or other communication lines. Output data of the microcontroller 225 is sent via a Bluetooth bi-direction radio communication port 245 to the CP 130. The Bluetooth portion 245 includes a Bluetooth communication interface, an antenna switch, and a related antenna, all of which allows wireless communication following the Bluetooth Special Interest Group standard. Other forms of wired and wireless communication between the PFD 145 and other components of the system including the CP 130 are also possible. Other outputs may include indicators (such as light-emitting diodes) for communicating stimulation activity 250, sensor activation 255, device power 260, and battery status 265.

The housing 400 of the PFD 145 may be cylindrical in shape (FIG. 1), and in one particular construction the cylinder is approximately 35 mm in diameter and 80 mm in length. In other constructions the cylinder is larger or smaller in diameter and/or length, for example in order to accommodate hands of varying sizes. In various constructions the diameter can range from 20 to 50 mm and the length from 30 to 120 mm, although other sizes above and below these ranges are also possible.

Furthermore, the shape of the PFD 145 can be other than a circular cross-section, for example oval, square, hexagonal, or other shape. Still further, the cross-section of the PFD 145 can vary along its length, for example being cylindrical in some portions and oval, square, hexagonal or other shape(s) in other portions. In yet other constructions, the PFD 145 has a spherical, toroid, or other shape.

The housing 400 may be made from a resilient material such as rubber or plastic with one or more sensor 205 coupled to or supported by the housing 400. The manner in which the sensor 205 is coupled to the housing 400 depends on the type of sensor that is employed, as discussed below. Thus, when the patient 105 applies a force to the housing 400, the sensor 205 generates a signal that generally is proportional to the degree of force applied. Although the discussion herein mentions the patient 105 using his or her hand to generate force to squeeze the housing 400 of the PFD 145, in various constructions the patient 105 may instead use other body parts, such as the mouth (FIG. 10) or foot (FIG. 12), to generate force. More generally, the patient can generate feedback by a physical action, usually a force applied by the hand or other body part, but the physical action can include other movements, such as movement of the patient's eyes (FIG. 9), head, or hands, to generate a feedback signal. After the signal is generated, it is transmitted from the sensor 205 to the controller 225. The controller 225 processes the signal and, based on one or more such signals from the sensor 205, the controller 225 generates another signal that is to be transmitted to the CP 130. The controller 225 sends the signal to be transmitted to the communication port 245 of the PFD 145 from which it is then transmitted to the CP 130 or other external device. As discussed further below, the signal can be transmitted from the communication port 245 to the CP 130 using various wired or wireless methods of communication.

In various constructions, an isotonic force sensor may include a sensor that measures the distance traveled by the sensor with relatively constant force applied by the patient. Isotonic force sensors may include a trigger 310 (FIG. 3) or other lever mechanism coupled to a wiper 320 that moves along a rheostat 330 or across a series of detectors. Exemplary detectors include electrical contacts or optical detectors, such as photodiodes. In other constructions, an isometric force sensor may include a strain gauge, a piezoelectric device, or a pressure sensor, 905 (FIG. 5) each of which measures force that is proportional to the pressure applied to the PFD 145 by the patient, generally with only a small amount of travel or shape change to the sensor. Both the isotonic and isometric sensors generate an electrical signal that is proportional to the force that is applied to the sensor. An isometric force sensor may be incorporated into a relatively stiff object such that only slight deformation of the object is needed to register a change in force. In still other constructions, the force sensor may include a combination of elements, such as a trigger or other lever that experiences increasing resistance or pressure as the travel distance increases. For example, increasing resistance or pressure can be created by attaching a relatively stiff spring to the lever or wiper mechanism to increase resistance as the lever or wiper is moved.

In some constructions (e.g. as shown in FIG. 4), the PFD 145 includes a feedback mechanism 460 that indicates to the patient 105 the amount of force that is detected by the force sensor 205. The feedback mechanism 460 may include one or more of a visual, audible, or tactile feedback mechanism that is used to indicate to the patient the degree to which the sensor 205 has been activated, e.g. how much force has been applied or how much the lever or wiper mechanism has traveled. The feedback mechanism gives the patient a sense of whether their activation of the sensor 205 is being detected at what the patient 105 feels is the correct level and to give the patient 105 a means to make their activation of the sensor 205 more consistent. Visual feedback mechanisms 460 can include a series of lights (e.g. LEDs) or a digital readout (e.g. a numerical display); audible feedback can include sounds that vary in amplitude (volume) and/or tone; and tactile feedback mechanisms can include vibration of the PFD 145 and/or altering the shape of the surface of the PFD 145 (e.g. raising of one or more structures such as dots to form Braille-type patterns) in a location that is capable of contacting the patient's skin. Using a combination of feedback modalities will benefit patients who have sensory impairments, including, e.g., impaired hearing and/or sight. The feedback can include a semi-quantitative indication of the patient's response, e.g. including a variety (e.g. 1-5 or 1-10) intensity levels to indicate a relative degree of force applied by the patient. The patient will then be able to see, hear, and/or feel the level of force that is sensed by the sensor 205 of the PFD 145, to help the patient 105 confirm that their response to the stimulus was received, as well as the degree of response that was registered. The correlation between the level of force applied and the output of the feedback mechanism 460 can be calibrated separately for each patient 105 during an initial calibration session.

To facilitate gripping of the PFD 145, the housing 400, in certain constructions, may be covered with one or more surfaces, textures, or materials to improve grip, such as grooves, stipples, indentations, rubber, or plastic, and may include a wrist strap 470 to keep the PFD 145 from falling if it is dropped by the patient.

The PFD 145, in some constructions, may also include a connection feedback mechanism, particularly where the PFD 145 is in wireless communication with the CP 130. The connection feedback mechanism can include one or more of a visual, audible, or tactile mechanism to inform the patient and/or medical personnel of whether the PFD 145 is maintaining a connection with the CP 130, the strength of the connection, and/or if the connection has been lost. For example, the PFD 145 may emit a signal (e.g. light, sound, and/or tactile) at regular (e.g. one minute) intervals to confirm that communication is still maintained. Conversely, the PFD 145 may emit such a signal only if communication is lost. In some constructions, the PFD 145 may tolerate brief intervals in which the signal is lost (e.g. a predetermined time, generally between 0.1-100 sec) before the patient is warned of a possible lost connection. In various constructions, the controller 225 of the PFD 145 includes memory that permits buffering of a limited amount of data, which can be used to accumulate data prior to sending to the CP 130 and which can hold data during brief intervals in which the connection is lost. In various constructions, if communication between the PFD 145 and the CP 130 is lost for more than a predetermined interval of time, then the CP 130 stops stimulation of electrodes until a connection with the PFD 145 is reestablished.

Thus, according to various constructions, the PFD 145 may include one or more of: a sound generating mechanism 420 (e.g. a speaker); a tactile mechanism 430 such as a vibration device and/or a mechanism for creating a raised pattern; a digital numerical readout 440 (e.g. LED or LCD display); and one or more indicator lights 450 (e.g. a series of LEDs); which may be employed to provide feedback to the patient 105 regarding the force being applied and/or communication status.

Various types of sensing mechanisms can be used for the sensor 205, which would depend in part on the type of housing 400 that is used with the PFD 145. For example, if the housing 400 is a sealed, flexible compartment (e.g. a ball or other object filled with gel, air, or liquid) a piezoelectric-based pressure sensing mechanism can be used as the sensor 205 in order to measure changes in pressure when the patient squeezes or relaxes his/her grip on the PFD 145. Alternatively, a rheostat 330 or other linear sensing mechanism can be used with a pistol grip style PFD 145 design (FIG. 3), where a trigger 310 is coupled to a wiper 320 that moves across the rheostat 330 or other linear sensor.

In another alternative shown in FIGS. 6 and 7, a strain gauge sensor can be used with a housing 400 that is sufficiently resilient to permit the housing to be deformed so as to activate the strain gauge. The strain gauge elements 480 (e.g. two elements for use with a half-bridge circuit and four elements for use with a full-bridge circuit) can be connected to the housing 400 in several different ways. The elements can be mounted directly to the housing 400, for example on opposing inside flat faces of the housing of the PFD 145, in which case the patient is instructed to squeeze the flat faces towards one another. Alternatively, the strain gauge elements can be mounted to opposite faces of a flexible element 490. The flexible element 490 may be a rectangular strip that is mounted across the inside, for example in a circular shape for mounting inside a cylindrical housing 400. In this particular construction, the flexible element 490 can be mounted inside the housing 400 perpendicular to the outer surface such that applying a force across any opposing sides of the PFD 145 causes the flexible element 490 to flex and thus trigger the strain gauge elements 480. This latter design would remove the requirement for the housing 400 to have opposing flattened faces that the patient would have to squeeze together.

Figure 8:
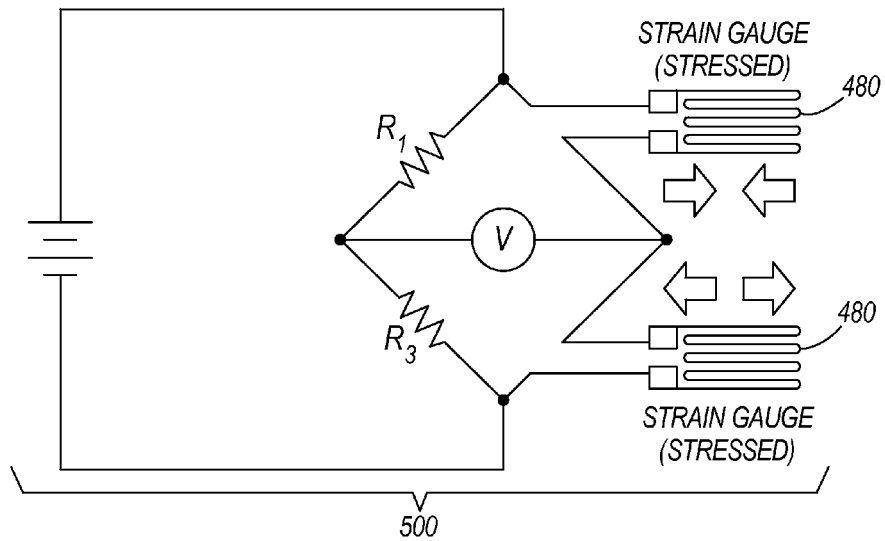
FIG. 8 is a diagram of a half bridge circuit coupled to two strain gauge elements.
Figure 9:
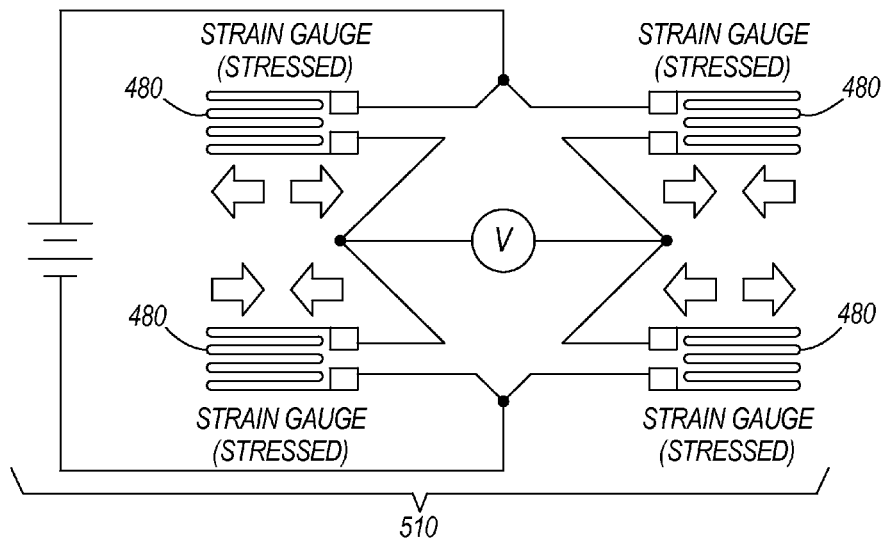
FIG. 9 is a diagram of a full bridge circuit coupled to four strain gauge elements.

In various constructions, two strain gauge elements 480 can be coupled to a half-bridge circuit 500 (FIG. 8), where the use of two elements 480 has the advantage of increasing the signal response as well as canceling out temperature variations in the PFD 145. Alternatively, four strain gauge elements 480 can be coupled to a full-bridge circuit 510 (FIG. 9). As discussed above, the two strain gauge elements 480 can be placed on the inside walls of the housing 400 or can be placed on opposite sites of a flexible element 490 that is mounted inside the housing 400 in a manner that causes the flexible element 490 to bend when a force is applied to the housing 400. The flexible element 490 may be various shapes (e.g. elongated or circular) and more than one flexible element 490 may be mounted inside the housing 400 to enhance the responsiveness of the PFD 145 to applied forces.

Figures 10, 11, 12:
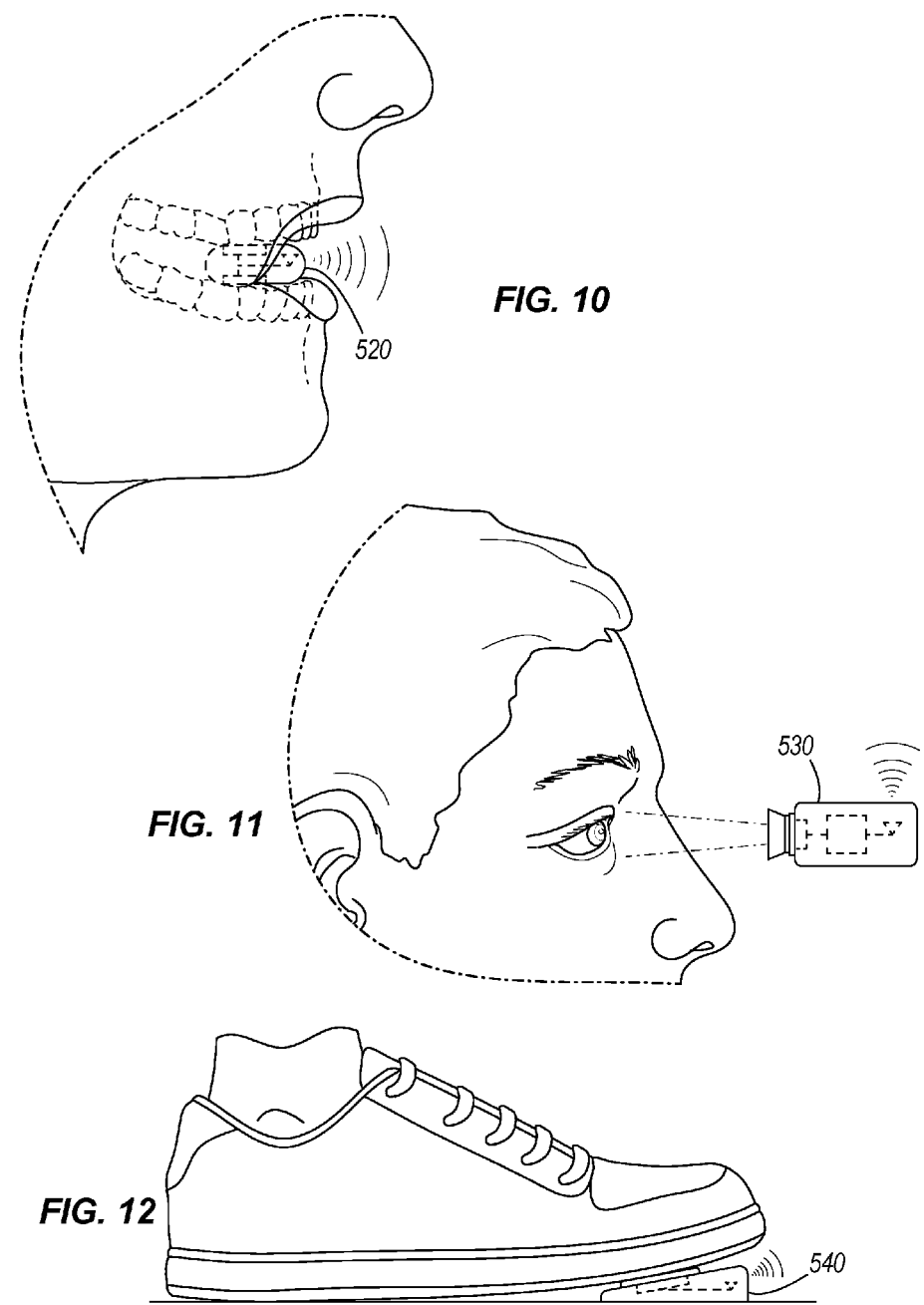
FIG. 10 is a side view of a patient-feedback device inserted in the mouth of a patient.
FIG. 11 is a side view of a patient-feedback device with optical sensing.
FIG. 12 is a side view of a patient-feedback device activated by a foot of a patient.

FIGS. 10-12 provide other means for receiving patient feedback. More specifically, FIG. 10 shows a mouth-piece 520 that is inserted into the mouth of the patient. The user provides feedback by biting the mouthpiece. FIG. 11 shows an optical sensor 530 (such as a camera and related image processing software) that detects visual cues from a patient. An example visual cue may be the blinking of the patient's eyes. FIG. 12 shows a foot pedal 540 that receives input through the patient's 105 manipulation of a switch and/or sensor with his foot. In other constructions the PFD 145 includes one or more accelerometer (such as the motion sensor 210) and the patient 105 provides feedback by moving the PFD 145 in various distinct patterns that are recognized by the controller 225 of the PFD 145 or by the CP 130. It is also envisioned that the patient may provide feedback directly to the CP 130. In various constructions, the patient 105 is trained to use the particular feedback device (e.g. the PFD 145 or the CP 130 as applicable) in order to properly inform the CP 130 of the patient's reaction to stimuli as they are applied to the IPG 115 in the patient 130. In particular constructions, the CP 130 is programmed to learn the patient's response times and/or the magnitude of the patient's responses in order to obtain a profile of the patient's reaction to various stimuli, as discussed above.

In some constructions the PFD 145 may include a clock 226 (e.g. as part of controller 225) that is synchronized with a clock in CP 130 so that as the patient 105 operates the PFD 145, each action recorded by the PFD 145 has a time associated therewith. Thus, even if there is a delay in transmitting information from the PFD 145 to the CP 130 (e.g. due to communication problems) there will nevertheless be an indication of when each action (e.g. squeezing of the PFD 145 leading to activation of the sensor 205) was recorded, which will enable the CP 130 to determine which of the most recent electrical stimuli likely led to the patient's response.

In some constructions, the PFD 145 can work without calibration in a relative or binary way. However, to facilitate identification of which of the stimuli the patient 105 has reacted to when using the PFD 145, the system 100, in some other constructions, includes procedures for calibrating the patient's response time and/or for 'learning' the patient's response time during ongoing use of the system 100. In one construction, the system 100 includes a calibration procedure in which the patient receives a signal or stimulus to apply pressure to the PFD 145 at time t=0. The actual times that the patient applies and releases pressure (e.g. squeezes the PFD 145 with his or her hand or other body portion) can then be compared and the difference between the signal time at t=0 and the time pressure is applied and released on the PFD 145 are indicators of the patient's response lag time. Knowing the lag time facilitates determining which particular electrical stimulus the patient 105 has responded to via the PFD 145. Although the discussion is presented in terms of the patient applying pressure or force, e.g. with his or her hand, the calibration or learning procedures discussed herein can be applied to other physical actions taken by a patient in response to a signal or stimulus, e.g. movements of the patient's head, eyes, or hands.

Steps of such a calibration procedure for a patient include: at a first time, applying a stimulus to the IPG 115 in the patient; monitoring the sensor 205 of the PFD 145 at a plurality of time points; recording a level of the force sensed by the sensor 205 at each of the plurality of time points; identifying at least one of a time point at which a maximum force is applied and a time point at which a minimum force is applied; comparing the first time to at least one of the time point at which a minimum force is applied and the time point at which a maximum force is applied to determine a patient response time; and recording the patient response time in a memory.

Analyzing the data generally includes identifying a local minimum or maximum of force, which can be done several ways. One method is to calculate the first derivative (dF/dt) of the force measurements over time to identify the time points at which force is applied (local maximum) and removed (local minimum). Another method is to apply a high-pass filter to the force vs. time data to identify local maxima and minima.

Still another method employs a learning algorithm to identify probabilities of maxima and minima based on the patient's use of the PFD 145. For example, after the patient 105 has squeezed the PFD 145 a number of times in response to electrode stimulation events and the system 100 has identified which stimulation event the patient was responding to, the system 100 can calculate an average lag time from the initial stimulation event to the patient's response thereto.

As discussed further below, the patient 105 provides feedback to the SCS system 100, and specifically the CP 130, while the CP 130 establishes the protocol for the IPG 115. The patient 105 can activate the PFD 145 when the patient 105 feels various stimuli, such as pain (or paresthesia).

Thus, in various constructions the invention provides a useful and novel system and method of providing patient feedback to a programming device of an electrical stimulation system.

What is claimed is:

1. A patient feedback device for communicating with a programming device of an electrical stimulation system to provide feedback during programming, the feedback device comprising:
    a housing;
    a sensor supported by the housing, the housing including an interface, the sensor generating a sensor signal in response to the interface being activated indicating a sensation experienced by the patient in response to electrical stimulation delivered to the patient;
    a communication port; and
    a controller supported by the housing and in operative communication with the sensor, the controller receiving the sensor signal and sending information to the communication port based on the sensor signal,
    wherein the communication port is connected to the housing and in operative communication with the controller, the communication port receiving information from the controller and wirelessly transmitting a communication signal to the programming device of the electrical stimulation system to provide feedback during programming.

2. The patient feedback device of claim 1, wherein the housing is resilient and the sensor generates the sensor signal in response to force applied to the housing.

3. The patient feedback device of claim 2, wherein the sensor comprises a strain gauge.

4. The patient feedback device of claim 1, further comprising a force feedback mechanism that is separate from the sensor, wherein the force feedback mechanism is configured to indicate to the patient an amount of force the patient applied to activate the interface.

5. A patient feedback device for communicating with a programming device of an electrical stimulation system to provide feedback during programming, the feedback device comprising:
    a resilient housing;
    a force sensor supported by the housing, the sensor generating a sensor signal in response to force applied to the housing by the patient;
    a communication port; and
    a controller supported by the housing and in operative communication with the force sensor, the controller receiving the sensor signal and sending information to the communication port based on the sensor signal,
    wherein the communication port is connected to the housing and in operative communication with the controller, the communication port receiving information from the controller and wirelessly transmitting a communication signal to the programming device of the electrical stimulation system to provide feedback during programming, and
    wherein the housing includes a force feedback mechanism that is separate from the force sensor, wherein the force feedback mechanism indicates to the patient the level of force applied to the housing.

6. The patient feedback device of claim 5, wherein the force feedback mechanism includes one or more of: a plurality of lights; a digital display; an audio output; and a tactile output.

7. The patient feedback device of claim 6, wherein the housing includes a connection feedback mechanism that indicates the status of the connection between the communication port and the programming device.

8. The patient feedback device of claim 7, wherein the connection feedback mechanism includes one or more of: a plurality of lights; a digital display; an audio output; and a tactile output.

9. The patient feedback device of claim 8, wherein the controller further comprises a controller clock and wherein the controller clock is synchronized with a clock in the programming device.

10. A method of providing patient feedback during programming to a programming device of an electrical stimulation system with a patient feedback device, the patient feedback device including a housing having an interface, a sensor, a controller, and a communication port connected thereto, wherein the controller is in operative communication with the sensor and the communication port, the method comprising:
    the interface receiving an impetus applied by the patient, the impetus indicating a sensation experienced by the patient in response to electrical stimulation delivered to the patient;
    the sensor generating a signal in response to the impetus;
    the controller receiving the signal generated by the sensor;
    the controller sending information to the communication port based on the signal;
    the communication port transmitting a signal to the programming device to provide feedback during programming.

11. The method of providing patient feedback of claim 10, wherein the housing is resilient and the method further comprises generating the sensor signal in response to a force applied to the housing.

12. The method of providing patient feedback of claim 11, wherein the step of the sensor generating a signal in response to the applied force further comprises the sensor generating a signal in response to the applied force using a strain gauge.

13. The method of providing patient feedback of claim 12, wherein the housing includes a force feedback mechanism and the method further comprises indicating, using the force feedback mechanism, the level of force applied to the housing.

14. The method of providing patient feedback of claim 13, wherein the step of indicating, using the force feedback mechanism, the level of force applied to the housing comprises indicating the level of force applied to the housing using one or more of: a plurality of lights; a digital display; an audio output; and a tactile output.

15. The method of providing patient feedback of claim 10, wherein the patient feedback device further comprises a connection feedback mechanism, and wherein the method further comprises indicating, via the connection feedback mechanism, the status of the connection between the communication port and the programming device at regular intervals using one or more of: a plurality of lights; a digital display; an audio output; and a tactile output.

16. The method of providing patient feedback of claim 15, wherein the controller further comprises a controller clock synchronized with a clock in the programming device, the controller receiving the signal generated by the sensor further comprising recording a time on the controller clock.

17. The method of providing patient feedback of claim 16, wherein the step of the communication port transmitting a signal to the programming device comprises the communication port transmitting a signal to the programming device using wireless communication.

18. A patient feedback device for communicating with a programming device of an electrical stimulation system to provide feedback during programming, the feedback device comprising:
 a resilient housing;
 a force sensor supported by the housing, the force sensor generating a sensor signal in response to an impetus applied to the housing by the patient;
 a communication port;
 a connection feedback mechanism; and
 a controller supported by the housing and in operative communication with the force sensor, the controller receiving the sensor signal and sending information to the communication port based on the sensor signal,
 wherein the communication port is connected to the housing and in operative communication with the controller, the communication port receiving information from the controller and transmitting a communication signal to the programming device of the electrical stimulation system to provide feedback during programming,
 wherein the housing includes a force feedback mechanism that is separate from the force sensor, the force feedback mechanism indicating a degree of force associated with the impetus applied to the housing; and
 wherein the connection feedback mechanism indicates the status of the connection between the communication port and the programming device at regular intervals.

19. The patient feedback device of claim 18, wherein the sensor comprises a strain gauge.

20. The patient feedback device of claim 18, wherein the force feedback mechanism includes one or more of: a plurality of lights; a digital display; an audio output; and a tactile output.

21. The patient feedback device of claim 20, wherein the communication port transmits the communication signal to the programming device using a wireless signal.

22. The patient feedback device of claim 18, wherein the connection feedback mechanism includes one or more of: a plurality of lights; a digital display; an audio output; and a tactile output.

23. The patient feedback device of claim 22, wherein the controller further comprises a controller clock and wherein the controller clock is synchronized with a clock in the programming device.

* * * * *